United States Patent [19]

Jegers

[11] Patent Number: 4,574,621
[45] Date of Patent: Mar. 11, 1986

[54] COMBINATION VISCOSITY MEASURING DEVICE AND STIRRER

[75] Inventor: Viktor J. Jegers, Bloomington, Minn.

[73] Assignee: Wagner Spray Tech Corporation, Minneapolis, Minn.

[21] Appl. No.: 623,968

[22] Filed: Jun. 25, 1984

[51] Int. Cl.⁴ ............................................. G01N 11/00
[52] U.S. Cl. ............................................ 73/54; 73/64.4
[58] Field of Search ................................... 73/54, 64.4

[56] References Cited

U.S. PATENT DOCUMENTS

| 2,054,438 | 9/1936 | Natelson | 73/64.4 |
| 2,638,778 | 5/1953 | Miller | 73/54 |
| 2,710,539 | 6/1955 | Pollack | 73/64.4 |
| 3,495,446 | 2/1970 | Williamson | 73/61.1 C |
| 4,135,100 | 1/1979 | Harada et al. | 250/573 |
| 4,142,402 | 3/1979 | Mattioli et al. | 73/61.2 |
| 4,228,678 | 10/1980 | Slaton | 73/64.4 |

FOREIGN PATENT DOCUMENTS

| 466653 | 9/1928 | Fed. Rep. of Germany | 73/64.4 |
| 642962 | 9/1946 | United Kingdom | 73/64.4 |

Primary Examiner—Jerry W. Myracle
Assistant Examiner—Hezron E. Williams
Attorney, Agent, or Firm—Hill, Van Santen, Steadman & Simpson

[57] ABSTRACT

A combination viscosity measuring device and stirrer has a handle portion and a shank portion, the shank portion having one or more apertures therein, the aperture or apertures being dimensioned so as to provide open span gradations. When the shank portion is dipped into and removed from a liquid whose viscosity is to be measured, the liquid will by surface tension form a film spanning one or more of the span gradations. The largest span gradation spanned by the liquid is a measurement of the viscosity of the liquid. The gradations are identified by designations so that a determination can be made as to whether the liquid has the proper viscosity for a particular application. In one embodiment the gradations may be in the form of a series of holes of different diameters, and in another embodiment the gradations may be in the form of a tapered slot.

10 Claims, 5 Drawing Figures

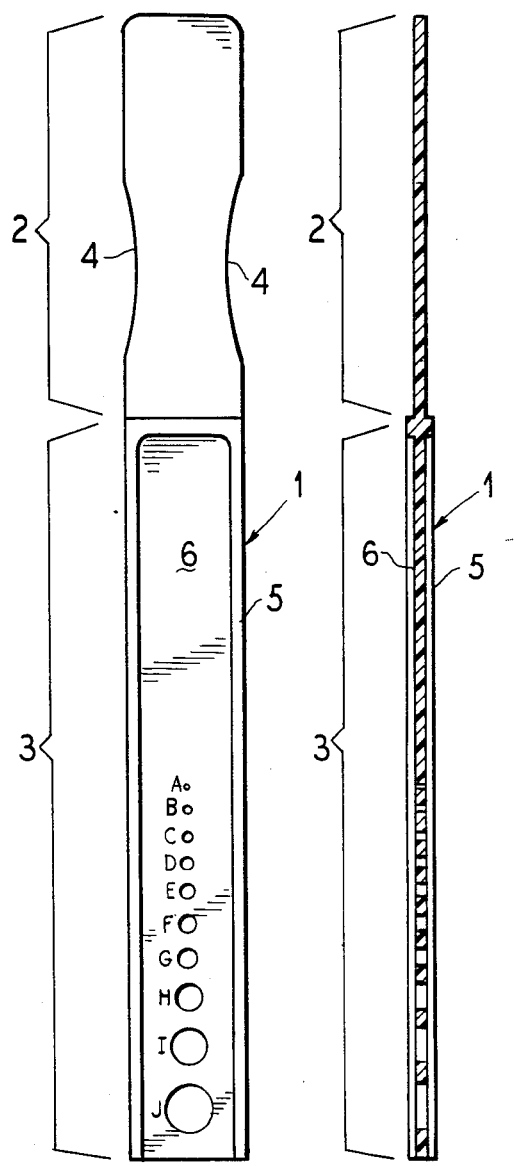
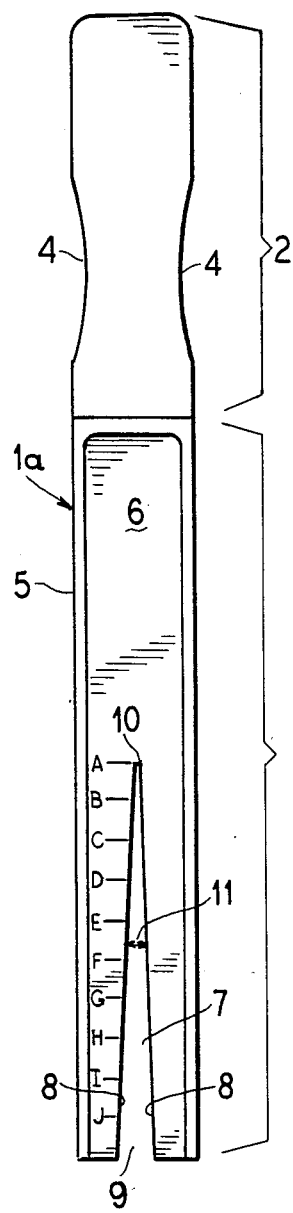
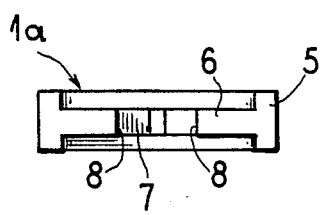
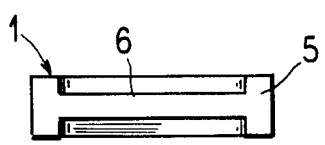
FIG. 4　　FIG. 1　　FIG. 3
FIG. 5　　FIG. 2

COMBINATION VISCOSITY MEASURING DEVICE AND STIRRER

BACKGROUND OF THE INVENTION

1. Field of the Invention

The present invention relates to a combination viscosity measuring device and stirrer, and in particular to such a device for measuring the viscosity and stirring fluid which is subsequently to be pumped and atomized in an airless sprayer.

2. Description of the Prior Art

Several types of devices are known in the art for measuring the viscosity of a fluid by measuring different properties of the fluid. A viscosity cup, for example, is described in U.S. Pat. No. 2,633,778 which measures the molecular shear forces within the fluid in which it is placed. Other types of devices measure the surface cohesion of the fluid by measuring the ability of the fluid to span an opening. Such a device is described, for example, in U.S. Pat. No. 4,228,678 wherein a disk having a plurality of spaced circular apertures of different diameters is rotated within a container holding a fluid whose viscosity is to be measured.

Another type of surface tension meter is disclosed in U.S. Pat. No. 2,710,539 which has a plurality of linearly disposed successive rings of varying diameters, the device being dipped into and removed from a liquid whose viscosity is to be measured with the largest ring opening which is covered by a film of the liquid being a measure of the viscosity of the liquid.

Another viscosity measuring device which measures surface tension or cohesion of the fluid is described in German Pat. No. 466,653. This device also has a plurality of linearly disposed circular apertures and is dipped into a liquid and removed therefrom thus leaving a thin web of fluid across a certain number of the apertures, the greater the degree of surface tension in the fluid, the larger the aperture which the fluid will span. The device disclosed in German Pat. No. 466,653 additionally is tapered so that a number of apertures having the same diameter, but different thicknesses, are also provided.

A problem exists in the painting technology in the use of airless sprayer units to apply fluid such as paint to a surface. Depending upon the design of the sprayer, the nature of the paint, and the coverage desired, proper viscosity of the paint which is supplied to the sprayer for pumping and atomization is important. Many applications may require the paint to be thinned before use with a particular sprayer.

SUMMARY OF THE INVENTION

It is an object of the present invention to provide an easily usable and readable viscosity measuring device for measuring the viscosity of fluid to be pumped and atomized in an airless sprayer.

It is a further object of the present invention to provide such a viscosity measuring device in combination with a structure for stirring the fluid whose viscosity is to be measured.

The above objects are inventively achieved in a combination viscosity measuring device and stirrer having a handle portion and an elongated shank portion, the elongated shank portion having a plurality of span gradations therein. The device is dipped into a fluid, such as a paint, whose viscosity is to be measured and removed therefrom, the greater the degree of surface tension in the fluid, the larger the span gradation which will be spanned by a thin film of fluid upon removal of the device therefrom.

In one embodiment, the span gradations are in the form of a plurality of circular apertures of the same thickness but different diameters. In another embodiment of the invention, the span gradations are in the form of a tapered or angled slot, with indicators being disposed adjacent the slot identifying different span gradations. The device can be used with instructions for particular types of sprayers or coverage desired, indicating the largest gradation which should be spanned by the fluid in order to ensure proper viscosity for a particular use.

The elongated structure, which is strengthened by ribs, permits the device to also be used as a stirrer to ensure that the fluid is of uniform mixture before undertaking a viscosity measurement.

DESCRIPTION OF THE DRAWINGS

FIG. 1 is a plan view of a first embodiment of a combination viscosity measuring device and stirrer constructed in accordance with the principles of the present invention.

FIG. 2 is an end view of the device shown in FIG. 1.

FIG. 3 is a sectional view taken aLong line III—III of FIG. 1.

FIG. 4 is a plan view of a second embodiment of the combination viscosity measuring device and stirrer constructed in accordance with the principles of the present invention.

FIG. 5 is an end view of the device shown in FIG. 4.

DESCRIPTION OF THE PREFERRED EMBODIMENTS

A combination viscosity measuring device and stirrer 1 is shown in various views in FIGS. 1-3. The combination device 1 has a handle portion 2 and an elongated shank portion 3. The handle portion 2 has a means for facilitating gripping thereof by a user in the form of opposed indentations 4.

The shank portion 3 has a continuous upraised frame 5 surrounding both sides and the top of the shank portion 3. A flat measuring and stirring surface 6 is disposed within the frame 5 and is completely surrounded thereby. The surface is recessed on both sides with respect to the frame 5, so that the frame 5 stiffens and supports the surface 6 to permit stirring of relatively highly viscus fluid, such as paint. The surface 6 has a plurality of span gradations in the form of circular apertures therein referenced A through J. Each aperture A through J is of a different diameter. The apertures A through J may have their respective centers aligned as shown in the drawings, however, it is not necessary to the inventive concept disclosed and claimed herein that the apertures be so aligned.

The respective diameters of the apertures A through J may be selected within ranges appropriate for measuring the viscosity of particular types of fluid. For measuring the viscosity of paint, for example, the pertures may have the following diameters, with the surface 6 having a preferred dimension of 0.18 inches (4.6 millimeters):

| Aperture | Diameter (Inches) | Diameter (Millimeters) |
| --- | --- | --- |
| A | .0520 | 1.32 |
| B | .0760 | 1.93 |
| C | .0995 | 2.53 |

-continued

| Aperture | Diameter (Inches) | Diameter (Millimeters) |
|---|---|---|
| D | .1250 | 3.18 |
| E | .1495 | 3.80 |
| F | .1730 | 4.39 |
| G | .2010 | 5.11 |
| H | .3020 | 7.67 |
| I | .4040 | 10.26 |
| J | .5000 | 12.70 |

The user of the combination device 1 stirs the fluid such as paint with the device so as to coat the surface 6. The user then removes the device 1 from the fluid, holding the device 1 vertically and waiting approximately 15 seconds until the web of fluid is formed across the largest aperture. The user notes the reference letter designating the aperture and, according to instructions provided with the paint of with a particular sprayer unit, if the web of paint is above a particular gradation the paint is adequate for spraying, however, if the web is below a designated gradation, thinning of the paint is required and the viscosity test is repeated.

Another embodiment of a combination viscosity measuring device and stirrer embodying the inventiove concept disclosed and claimed herein is shown in FIGS. 4 and 5 referenced 1a. The combination device 1a also has a handle portion 2 with opposed indentations 4 and an elongated shank portion 3 having a frame 5 surrounding a stirring and measuring surface 6. In this embodiment, the span gradations are in the form of a tapered or angled slot 7 in the surface 6. The tapered slot 7 has straight angled sides 8 and an open end 9 at a bottom of the deice 1a. The sides 8 intersect at an apex 10. The span gradations A through J are indicated along one of the sides 8 at intervals.

In a preferred embodiment, the distance from the apex 10 to the open end 9 is approximately 4 inches (101.6 millimeters) and is divided into 10 equal intervals by 10 gradations A through J, so that each gradation is spaced from its adjacent gradations by appromimately 0.4 inches (10.16 millimeters). In this preferred embodiment, the thickness of the surface 6 is again approximately 0.18 inches (4.6 millimeters) and the angle 11 of the slot 7 is approximately 5.5°.

The second embodiment of the combination device 1a is used identically as described above for the combination device 1. The device 1a is used to stir fluid such as paint and is then removed from the fluid and held vertically until a web of paint has formed extending down to a lowest gradation. The reference identifier closest to the meniscus of the web is determined and from this reading the user can determine whether the paint is adequate for spraying, or whether thinning is necessary.

Although modifications and changes may be suggested by those skilled in the art, it is the intention of the inventor to embody within the patent warranted hereon all changes and modifications as reasonably and properly come within the scope of his contribution to the art.

I claim as my invention:

1. A combination viscosity measuring device and stirrer for measuring the viscosity of and stirring a fluid comprising:
   a handle portion adapted for gripping;
   an elongated shank portion connected to said handle portion; and
   a rigid flat stirring and measuring surface disposed within said shank portion having a tapered slot with a plurality of open span gradations therein of different span sizes at selected intervals along said slot, said surface being stiffened and having a width substantially less than its length for stirring said fluid as said shank portion is moved therethrough by said handle,
   whereby said shank portion is moved through a fluid by a user gripping said handle portion for stirring said fluid and is subsequently removed from said fluid for permitting a web of said fluid to form across a number of said span gradations, a largest of said span gradations spanned by said fluid indicating the viscosity of said fluid.

2. A combination viscosity measuring device and stirrer as claimed in claim 1 further comprising:
   a stiffening frame carried on said shank portion at least partially surrounding said measuring and stirring surface.

3. A combination viscosity measuring device and stirrer as claimed in claim 1 wherein said intervals are equal.

4. A combination viscosity measuring device and stirrer as claimed in claim 1 wherein said slot is open at one end thereof.

5. A combination viscosity measuring device and stirrer as claimed in claim 1 wherein said tapered slot is tapered at an angle of approximately 5.5°.

6. A combination viscosity measuring device and stirrer as claimed in claim 1 further comprising a plurality of visual indicators disposed on said stirring and measuring surface respectively adjacent said intervals.

7. A combination viscosity measuring device and stirrer as claimed in claim 1 wherein said stirring and measuring surface is of uniform thickness.

8. A combination viscosity measuring device and stirrer as claimed in claim 1 wherein said handle portion is adapted for gripping by a pair of opposed indentations in said handle portion.

9. A combination viscosity measuring device and stirrer comprising:
   a handle portion adapted for gripping;
   an elongated shank portion connected to said handle portion;
   a frame at least partially surrounding said shank portion;
   a rigid flat measuring and stirring surface of uniform thickness carried on said shank portion within said frame and having a width substantially less than the length; and
   a tapered slot open at one end disposed in said measuring and stirring surface,
   whereby said handle is utilized for moving said shank portion through a fluid, said shank portion being subsequently vertically removed from said fluid for permitting a web of said fluid to form across a portion of said tapered slot, a greatest width of said tapered slot which is spanned by said web of fluid indicating the viscosity of said fluid.

10. A combination viscosity measuring device and stirrer as claimed in claim 9 further comprising at least one indicator on said measuring and stirring surface adjacent said tapered slot designating a selected position for comparison with the position of said web at said greatest width spanned by said web.

* * * * *